United States Patent [19]

Bromidge et al.

[11] Patent Number: 5,110,828

[45] Date of Patent: May 5, 1992

[54] AZABICYCLO OXIME DERIVATIVES

[75] Inventors: Steven M. Bromidge; Michael S. Hadley; Barry S. Orlek, all of Harlow, England

[73] Assignee: Beecham Group p.l.c., Brentford, England

[21] Appl. No.: 337,281

[22] Filed: Apr. 13, 1989

[30] Foreign Application Priority Data

Apr. 15, 1988 [GB] United Kingdom ............... 8808925
May 27, 1988 [GB] United Kingdom ............... 8812602
Oct. 13, 1988 [GB] United Kingdom ............... 8824076

[51] Int. Cl.$^5$ .................. C07D 453/02; A61K 31/435
[52] U.S. Cl. ................................. 514/413; 514/183; 514/214; 514/299; 514/305; 540/477; 540/582; 546/112; 546/133; 548/453
[58] Field of Search ............... 546/112, 133; 548/453, 548/950; 514/210, 413, 299, 305, 214, 183; 540/477, 582

[56] References Cited

U.S. PATENT DOCUMENTS 4,710,508 12/1987 Bergmeier et al. .................. 514/357
4,927,837 5/1990 Galliani et al. ...................... 514/331
4,937,239 6/1990 Lauffer et al. ...................... 514/214

FOREIGN PATENT DOCUMENTS 0094742 11/1983 European Pat. Off. .
0239445 9/1987 European Pat. Off. .
0257741 3/1988 European Pat. Off. .
0261763 3/1988 European Pat. Off. .
0271798 6/1988 European Pat. Off. .
0287356 10/1988 European Pat. Off. .
0288394 10/1988 European Pat. Off. .
0291673 11/1988 European Pat. Off. .
0308283 3/1989 European Pat. Off. .
0308284 3/1989 European Pat. Off. .
0316718 5/1989 European Pat. Off. .

OTHER PUBLICATIONS

March, J., *Advanced Organic Chemistry*, McGraw Hill, New York, 1968, p. 675.

Primary Examiner—Mary C. Lee
Assistant Examiner—Lenora Mittenberger
Attorney, Agent, or Firm—Hopgood, Calimafde, Kalil, Blaustein & Judlowe

[57] ABSTRACT

Novel compounds of formula (I), a process for their preparation, and their use as pharmaceutical agents are described:

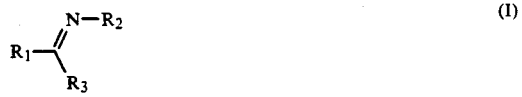

wherein $R_1$ represents

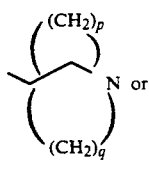

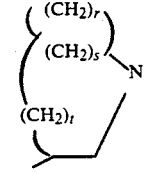

in which
each of p and q independently represents an integer of 2 to 4, r represents an integer of 2 to 4, s represents 1 or 2 and t represents 0 or 1;
$R_2$ is a group $OR_4$, where $R_4$ is $C_{1-4}$ alkyl, $C_{2-4}$ alkenyl, $C_{2-4}$ alkynyl, a group $OCOR_5$ where $R_5$ is hydrogen or $R_4$, or a group $NHR_6$ or $NR_7R_8$ where $R_6$, $R_7$ and $R_8$ are independently $C_{1-2}$ alkyl; and
$R_3$ is hydrogen or $C_{1-4}$ alkyl, subject to the proviso that when $R_2$ is a group $OCOR_5$ or a group $NHR_6$, $R_3$ is $C_{1-4}$ alkyl.

9 Claims, No Drawings

AZABICYCLO OXIME DERIVATIVES

This invention relates to compounds having pharmaceutical activity, to a process for their preparation and their use as pharmaceuticals.

EP-A 0257741 (Beecham Group p.l.c.) discloses certain azabicyclic compounds which enhance acetylcholine function via an action at muscarinic receptors within the central nervous system.

A novel group of compounds has now been discovered which also enhance acetylcholine function via an action at muscarinic receptors within the central nervous system and are therefore of potential use in the treatment and/or prophylaxis of dementia in mammals.

According to the present invention, there is provided a compound of formula (I) or a pharmaceutically acceptable salt thereof:

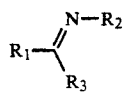
(I)

wherein $R_1$ represents

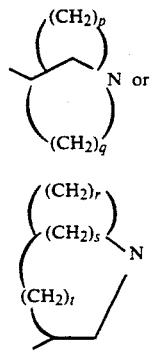

in which
each of p and q independently represents an integer of 2 to 4, r represents an integer of 2 to 4, s represents 1 or 2 and t represents 0 or 1;

$R_2$ is a group $OR_4$, where $R_4$ is $C_{1-4}$ alkyl, $C_{2-4}$ alkenyl, $C_{2-4}$ alkynyl, a group $OCOR_5$ where $R_5$ is hydrogen or $R_4$, or a group $NHR_6$ or $NR_7R_8$ where $R_6$, $R_7$ and $R_8$ are independently $C_{1-2}$ alkyl; and $R_3$ is hydrogen or $C_{1-4}$ alkyl, subject to the proviso that when $R_2$ is a group $OCOR_5$ or $NHR_6$, $R_3$ is $C_{1-4}$ alkyl.

Compounds of formula (I) are capable of existing in a number of stereoisomeric forms including geometric isomers and, for certain compounds, enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

It is preferred that compounds of formula (I) having two assymetric centers have the stereo-chemical configuration in which the group $-C(R_3)=NR_2$ and the $(CH_2)_s$ bridge are on the same side of the plane of the molecule which contains both bridgehead atoms and the ring carbon atom bonded to the aforesaid group. This configuration will hereinafter be referred to as the exo configuration.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

Preferably, p and q each independently represents 2 or 3. Most preferably p represents 2 and q represents 2 or 3.

Preferred combinations of (r,s,t) include (2,2,0), (2,1,1), (3,1,1), (2,1,0) and (3,1,0).

The groups $R_4$ and $R_5$ in $R_2$ are preferably selected from methyl, ethyl, allyl and propargyl. $R_6$, $R_7$ and $R_8$ are preferably methyl. Suitable examples of $R_2$ include methoxy, ethoxy, allyloxy, propargyloxy, acetoxy and dimethylamino.

When $R_2$ is a group $OR_4$ or $NR_7R_8$, $R_3$ is preferably hydrogen or methyl.

When $R_2$ is a group $OCOR_5$ or $NHR_6$, $R_3$ is preferably methyl.

The invention also provides a process for the preparation of a compound of formula (I), or a pharmaceutically acceptable salt thereof, which process comprises reacting a compound of formula (II):

(II)

with a compound of formula (III):

$$R_2'-NH_2 \quad (III)$$

wherein $R_2'$ represents $R_2$ or hydroxy, converting $R_2'$ to $R_2$ when hydroxy, and thereafter forming a pharmaceutically acceptable salt.

The reaction between the compounds of formulae (II) and (III) is preferably carried out in a hydroxylic solvent such as methanol or ethanol, at ambient temperature, or where appropriate, at elevated temperature.

Where $R_2$ in compounds of formula (I) is a group $OR_4$, $NHR_6$ or $NR_7R_8$, a compound of formula (II) is conveniently reacted with a compound of formula (III) in which $R_2'$ is $R_2$.

Where $R_2$ in compounds of formula (I) is a group $OCOR_5$, a compound of formula (II) may be reacted with the compound of formula (III) in which $R_2'$ is hydroxy, with subsequent acylation of the resulting oxime by treatment with a suitable acylating agent such as an acyl halide, for example acetyl chloride.

Compounds of formula (II) where $R_1$ is

Compounds of formula (II) where $R_1$ is 

may conveniently be prepared by cyclizing a compound of formula (IV):

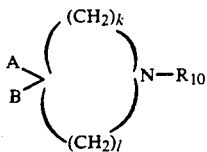
(IV)

in which (i) A represents $COR_3$ or a group convertible thereto and B represents —$(CH_2)_jL_1$ where $L_1$ is a leaving group or A and $L_1$ together represent —COO—; one of j, k and l is 1 and the other two independently represent an integer of 2 to 4, and $R_{10}$ represents hydrogen or an N-protecting group; to give a compound of formula (IVa):

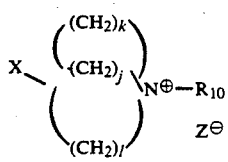
(IVa)

in which X represents $COR_3$ or a group convertible thereto, $Z^\ominus$ is an anion and the remaining variables are as previously defined;

or (ii) A represents an electron withdrawing group, B represents hydrogen and $R_{10}$ represents —$(CH_2)_j L_2$ where $L_2$ is a leaving group; one of k and l is 1 and the other and j independently represent an integer of 2 to 4; to give a compound of formula (IVb):

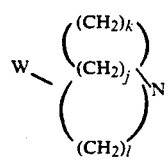
(IVb)

in which W represents an electron withdrawing group or X and the remaining variables are as previously defined;

and thereafter, optionally or as necessary, removing any $R_{10}$ N-protecting group, converting W to X and converting X to $COR_3$.

The deprotection, conversion and interconversion steps may be carried out in any appropriate order.

Examples of the leaving groups $L_1$ and $L_2$ include halo such as bromo or chloro, tosyloxy and mesyloxy.

Examples of $R_{10}$ when an N-protecting group include benzyl and substituted benzyl.

Examples of A and X when groups convertible to $COR_3$ include alkoxycarbonyl, benzyloxycarbonyl and cyano.

The cyclization reaction is a nucleophilic substitution which may be carried out under conventional conditions appropriate to the groups A and B. Thus, when B is $(CH_2)_jBr$ and A is $C_{1-4}$ alkoxycarbonyl, the cyclization is carried out in an inert solvent such as toluene or ether at elevated temperature. When B is $(CH_2)_jOTos$ or $(CH_2)_jOMes$, it is preferably obtained by treatment of a $(CH_2)_jOH$ group with a suitable reagent such as tosyl chloride or mesyl chloride, in a base such as pyridine, whereupon the cyclization may proceed at ambient temperature, or at elevated temperature in an inert solvent such as toluene. When A and $L_1$ together represent —COO—, the cyclization may be carried out in a lower alkanol such as ethanol in the presence of acid such as hydrogen bromide. In the resulting compound of formula (IVa), X will be an alkoxycarbonyl group corresponding to the lower alkanol used for the cyclization.

Where $R_{10}$ is an N-protecting group such as benzyl, this may be removed by conventional hydrogenation, preferably catalytically over a suitable catalyst such as Pd/C.

Examples of A when an electron withdrawing group include $C_{1-4}$ alkoxycarbonyl and cyano.

When A is an electron withdrawing group such as $C_{1-4}$ alkoxycarbonyl, B is hydrogen and $R_{10}$ is —$(CH_2)_jL_2$ where $L_2$ is, for example, chloro, the cyclization may be effected by treatment of the compound of formula (II) with lithium diisopropylamide.

Compounds of formula (II) where $R_1$ is 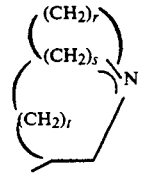

may conveniently be prepared by:
(a) cyclizing a compound of formula (Va):

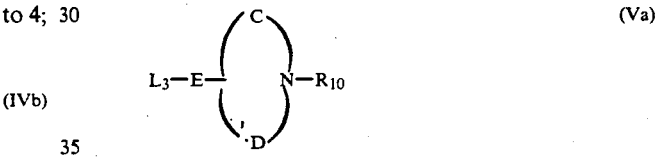
(Va)

where $R_{10}$ is hydrogen or an N-protecting group, and either C is one, D is another and E is the remainder of —$(CH_2)_r$—, —$(CH_2)_s$— and —$(CH_2)_t$—CHX—$CH_2$— or groups convertible thereto, X is $COR_3$ or a group convertible thereto and $L_3$ is a leaving group, or C is one and E is the other of —$(CH_2)_r$— and —$(CH_2)_s$— or groups convertible thereto and D represents —$(CH_2)_t$—CHX—$CH_2$— where X and $L_3$ together represent —COO—, and thereafter, optionally or as necessary and in any appropriate order, converting C, D and E to —$(CH_2)_r$—, —$(CH_2)_s$— and —$(CH_2)_t$—CHX—$CH_2$—, removing any $R_{10}$ protecting group, and converting X to $COR_3$; or (b) cyclizing a compound of formula (Vb):

(Vb)

where F is one and G is the other of —$(CH_2)_r$— and —$(CH_2)_s$— or groups convertible thereto, and one of $Y^3$ and $Y^4$ is —$(CH_2)_m$—W and the other is —$(CH_2)_n$-$(CO)_xL_4$ where W is an electron withdrawing group, $L_4$ is a leaving group, m is 1 or 2, n is 0 or 1 and x is 0 or 1, with the proviso that, when $Y^4$ is —$(CH_2)_n$-$(CO)_xL_4$, n and x are each 1, and thereafter, optionally or as necessary and in any appropriate order, hydrolyzing and decarboxylating the cyclization product and converting the carbonyl group to —CHX where X is COR$_3$ or a group convertible thereto, converting W to X as defined, converting X to COR$_3$, converting F and G to —(CH$_2$)$_r$— and —(CH$_2$)$_s$— as appropriate, m, n and x being such that the desired compound of formula (II) is obtained.

Examples of leaving groups L$_3$ include halo such as chloro and hydroxy. Examples of L$_4$ include those given for L$_3$ or, when x is 1, C$_{1-4}$ alkoxy such as ethoxy. Examples of electron withdrawing groups W include C$_{1-4}$ alkoxycarbonyl and cyano. In the group —(CH$_2$)$_r$—CHX—CH$_2$—, examples of X include hydroxy and cyano.

In the process variant (a), where L$_3$ is hydroxy and D is —CHOH—CH$_2$—, the cyclization may be carried out by pyrolysis, by the method of D. O. Spry and H. S. Aaron, J. Org. Chem., 1969, 34. 3674, to yield a compound where X is hydroxy.

Where E is —(CH$_2$)$_t$COCH$_2$—, the cyclization may be carried out under basic conditions where R$_{10}$ is benzyl (F. I. Carrol, A. M. Ferguson, and J. B. Lewis, J. Org. Chem. 31. 2957, 1966). The resulting ketone may be reacted with tosylmethyl isocyanide to yield a compound where X is cyano.

Where L$_3$ and X together represent —COO—, the cyclization is a rearrangement reaction which can be carried out under acid conditions in a polar solvent, such as hydrogen bromide in ethanol, at ambient temperature, to yield a compound where X is a carboxy ester group. It is preferred to protect the nitrogen atom with an R$_{10}$ N-protecting group such as benzyl, which may be subsequently removed by hydrogenation over a suitable catalyst such as Pd/C.

In the process variant (b), where Y$^3$ and Y$^4$ both contain carboxy ester groups the cyclization is a Dieckmann reaction which is catalyzed by a base such as potassium t-butoxide at elevated temperature in a solvent such as toluene.

The resulting β-keto ester is hydrolyzed and decarboxylated under conventional conditions such as heating at reflux in dilute hydrochloric acid.

The carbonyl group may then be reduced to an X hydroxy group with a suitable reducing agent such as sodium borohydride in ethanol at ambient temperature, or sodium in ethanol at elevated temperature, such as the boiling point of the solvent, under an inert atmosphere such as nitrogen, depending upon the stereochemistry required.

Alternatively, the carbonyl group may be converted directly to an X cyano group with a suitable reagent such as tosylmethylisocyanide in an inert solvent such as dry dimethoxyethane, at depressed temperature, under basic conditions such as the presence of potassium t-butoxide.

Where x is 1, cyclization may be carried out as described in EP-A-... under basic conditions such as sodium hydride and potassium t-butoxide, in an inert polar solvent such as dimethyl formamide.

The conversion of W and X to COR$_3$ may be carried out conventionally.

An X hydroxy group may be converted to cyano by first converting it to a good leaving group such as mesyloxy or tosyloxy and then displacing it with cyanide ion.

An X carboxy group may be obtained by conventional de-esterification of an X or W alkoxycarbonyl group. Where R$_{10}$ is an N-protecting group and X or W is a benzyloxycarbonyl group, the de-esterification and deprotection steps may conveniently be effected simultaneously by conventional hydrogenation such as described above. Alternatively, an X carboxy group may be obtained by conventional acid hydrolysis of an X or W cyano group. A carboxy group may be treated with thionyl chloride at elevated temperature to give a chlorocarbonyl group.

An R$_3$CO— group may be obtained from an X or W cyano group by treatment with the appropriate alkyl lithium in ether at depressed temperature, or by treatment of a LiOOC group with an alkyl lithium, the LiOOC group being obtained by hydrolysis of an X or W alkoxycarbonyl group with lithium hydroxide in water. Alternatively, an R$_3$CO— group may be obtained by reaction of a chlorocarbonyl group with N,O-dimethylhydroxylamine and treatment with an alkyl lithium.

An X or W cyano or carboxylic acid derivative group such as alkoxycarbonyl or N-methoxy-N-methylamido may be converted to —CHO by controlled reduction using a suitable reducing agent such as diisobutylaluminium hydride in an inert solvent such as toluene at low temperature.

Alternatively an X —CHO group may be obtained by treatment of a carbonyl group with methoxymethyl triphenylphosphonium chloride in the presence of a base such as potassium t-butoxide in a suitable dry solvent such as tetrahydrofuran. The resulting enol ether can be hydrolyzed to give the required aldehyde using an acid such as sulphuric acid or perchloric acid.

Compounds of formula (IV) may be prepared conventionally.

Where A is C$_{1-4}$ alkoxycarbonyl, B is (CH$_2$)$_j$L$_1$ and R$_{10}$ is hydrogen or an N-protecting group, the compound of formula (IV) may be prepared by treating a compound of formula (VI):

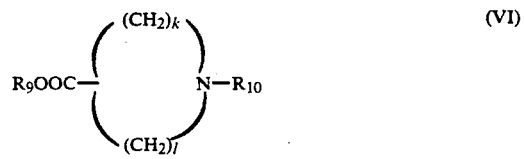

where R$_9$ is C$_{1-4}$ alkyl and the remaining variables are as previously defined, with lithium diisopropylamide, prepared in situ from diisopropylamine and n-butyllithium followed by reaction with a compound L$_5$(CH$_2$)$_r$L$_1$ where L$_5$ is a leaving group, in an inert solvent such as ether at depressed to elevated temperature. Both L$_1$ and L$_5$ are suitably bromo.

Where A and L$_1$ together represent —COO— and j is 2, the compound of formula (IV) may be prepared by reacting the compound of formula (VI), treated with lithium diisopropylamide as before, with ethylene oxide in an inert solvent such as ether at depressed to elevated temperature.

Where A is an electron withdrawing group such as C$_{1-4}$ alkoxycarbonyl, B is hydrogen and R$_{10}$ is (CH$_2$)$_j$L$_2$, the compound of formula (IV) may be prepared by reacting the compound of formula (VI) where R$_{10}$ is hydrogen with a compound L$_5$(CH$_2$)$_j$L$_2$ where L$_5$ is as previously defined, in a solvent such as acetone in the presence of a base such as potassium carbonate. The leaving group L$_5$ is preferably bromo and L$_2$ is preferably chloro.

Compounds of formula (VI) are known compounds or may be prepared by analogous methods to those for preparing known compounds. The compound of formula (VI) where k is 2, l is 1 and $R_{10}$ is benzyl may be prepared by the cyclization of di-$C_{1-4}$ alkyl itaconate in the appropriate alkanol with benzylamine at elevated temperature, followed by reduction of the resulting oxo group at the 2-position of the pyrrolidine ring with $BH_3$ in tetrahydrofuran, at ambient to elevated temperature.

Intermediates of formulae (Va) and (Vb) are known compounds (e.g. as described in EP-A-0094742) or may be prepared analogously.

Intermediates of formula (Va) where X and $L_3$ together represent —COO— are described in, for example, Kuthan et al., Coll. Czechoslov. Chem. Comm., 1977, 42, 283 or may be prepared therefrom by conventional hydrogenation of the pyridine ring over 5% Pt/C, and benzylation of the nitrogen atom by treatment with benzyl bromide and potassium carbonate in dry acetone.

Intermediates of formula (Va) where $L_3$ is a leaving group are described in, for example, Spry et al., J. Org. Chem., 1969, 34, 3674 and Hasse et al., Chem. Ber., 1960, 93, 1686.

Intermediates of formula (Vb) are described in, for example, Martell et al., J. Pharm. Sci., 1963, 52(4), 331, Sternbach et al., J.A.C.S., 1952, 74, 2215, Thill et al., J. Org. Chem., 1968, 33, 4376 and EP-A 0094742.

Compounds of formula (III) are known compounds or may be prepared by analogous methods to those for preparing known compounds. Certain compounds of formula (III) are commercially available.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, or hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavoring or coloring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10%–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50 mg; and such unit doses may be administered more than once a day, for example two or three times a day, so that the total daily dosage is in the range of about 0.01 to 5 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

Description 1

(±) Ethyl 1-(2-chloroethyl)-3-piperidylcarboxylate (D1)

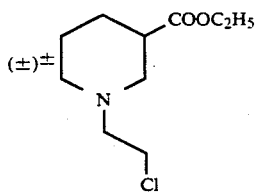

A solution of ethyl 3-piperidylcarboxylate (100g, 0.64 mole) in acetone (800ml) was treated with 1-bromo-2-chloroethane (106.5 ml, 1.28 mole) and anhydrous potassium carbonate (138g, 1.00 mole) and the mixture stirred at room temperature for 24 h. The mixture was concentrated in vacuo and the residue treated with water (300 ml) and extracted with ether (2 ×200 ml). The combined ether extracts were dried ($Na_2SO_4$) and concentrated in vacuo to leave a yellow oil, which was purified by chromatography on silica gel eluting with 50% ether/60-80 petrol to give the title compound (D1) as a pale yellow oil (78.2g, 56%). $^1$H Nmr ($CDCl_3$) δ: 1.25 (3H, t, J=7Hz), 1.40-3.10 (11H, m), 3.58 (2H, t, J=7Hz), 4.15 (2H, q, J=7Hz).

Description 2

(±) Ethyl 1-azabicyclo[3.2.1]oct-5-ylcarboxylate (D2)

A solution of diisopropylamine (33.6 ml, 0.24 mole) in dry ether (1500 ml) at −65° C. under nitrogen was treated with 1.5 M n-butyllithium in hexane (150 ml, 0.225 mole) and the solution stirred for 15 mins, before adding N,N,N',N'-tetramethylethylenediamine (68 ml, 0.45 mole). After stirring for a further 15 mins, the solution was treated with a solution of (±) ethyl 1-(2-chloroethyl)-3-piperidylcarboxylate (D1, 44.7g, 0.204 mole) in dry ether (100 ml) and the mixture allowed to warm up to room temperature over 2 h. The 2 reaction mixture was treated with potassium carbonate solution (300 ml) and the ether layer separated, dried ($Na_2SO_4$) and concentrated in vacuo to leave an orange oil. This was purified by chromatography on silica gel eluting with 10% methanol/chloroform to give the title compound (D2) as a yellow oil (31.9 g, 84%), b.p. 120° C.-130° C. at 0.4 mm (Kugelröhr apparatus). $^1$H Nmr ($CDCl_3$) δ: 1.25 (3H, t, J=7Hz), 1.10-2.20 (6H, m), 2.60-3.25 (6H, m), 4.20 (2H, q, J=7Hz).

Description 3

(±) 1-Azabicyclo[3.2.1]oct-5-ylcarboxaldehyde (D3)

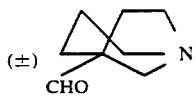

A solution of (±) ethyl 1-azabicyclo[3.2.1]oct-5-ylcarboxylate (D2, 6.0 g, 0.033 mole) in dry toluene (150 ml) at −65° C. under nitrogen was treated dropwise over 15 minutes with 1.5 M diisobutylaluminium hydride in toluene (30 ml, 0.045 mole) and the reaction stirred at −65° C. for 1.25 h. The solution was poured into 10% sodium hydroxide solution (100 ml), stirred for 5 minutes and then extracted with ethyl acetate (1×150 ml) followed by chloroform (1×100 ml). The two extracts were dried ($Na_2SO_4$) and concentrated in vacuo separately. The ethyl acetate extract gave a gelatinous white semi-solid, which was shaken with ether (200 ml), filtered through a pad of kieselguhr and the filtrate concentrated in vacuo to leave a pale yellow oil. This was combined with the product from the chloroform extract to give a yellow oil (5.0 g) containing the title compound (D3), which was used without further purification.

Description 4

(±) 3-Cyano-1-azabicyclo[2.2.2]octane (D4)

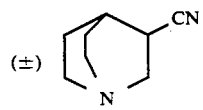

A mixture of 3-quinuclidinone (12.5 g; 0.10 moles), tosylmethyl isocyanide (25.4 g; 0.13 moles) and dry ethanol (10 ml; 0.17 moles) in dry dimethoxyethane (350 ml) was cooled in ice and treated portionwise with potassium t-butoxide (28.0 g; 0.25 moles) while maintaining the temperature between 5° C. and 10° C. After addition was complete the ice bath was removed and stirring was continued for a further 30 min. The reaction was then heated at 40° C. for 2.5 h. After cooling the precipitate was filtered off and the filtrate concentrated in vacuo. Purification on neutral alumina (Brockmann grade 1) using 2% methanol in ethyl acetate as eluant afforded the title compound (D4) as a syrup (10.0 g; 74%) which crystallized on cooling.

Description 5

(±) 1-Azabicyclo[2.2.2]oct-3-ylcarboxaldehyde (D5)

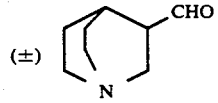

A stirred solution of (±) 3-cyano-1-azabicyclo[2.2.2]-octane (D4, 2.1 g, 0.0154 mole) in dry toluene (50 ml) was cooled to −65° C. under nitrogen and treated over 20 minutes with a 1.5 M solution of diisobutylaluminium hydride in toluene (13.3 ml, 0.020 mole). The solution was stirred at this temperature for 20 minutes, then allowed to warm up to room temperature over 2 h, before adding 10% sodium hydroxide solution (50 ml) and extracting with chloroform (3×60 ml). The combined organic extracts were dried (Na2SO4) and concentrated in vacuo to give a beige semi-solid (2.3 g), of which approximately 50% was the title compound (D5). The majority of the remaining 50% was starting material (D4). This mixture was used without purification.

Description 6

(±) 3-Acetyl-1-azabicyclo[2.2.2]octane (D6)

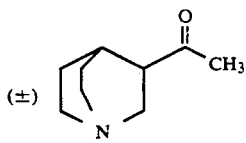

To a solution of (±) 3-cyano-1-azabicyclo[2.2.2]octane (D4, 10.0 g; 0.07 mole) in dry ether (125 ml) cooled to 0° C. under nitrogen was added methyl lithium (67 ml of a 1.5 M solution in ether; 0.10 mole) over 15 min. After 2 h at 0° C. the reaction was quenched with 125 ml of 5 N sulphuric acid and stirred for a further 3 h at ice temperature. After separation of the ether layer, the aqueous phase was saturated with potassium carbonate and extracted into chloroform (4×100 ml). The combined extracts were dried (Na2SO4) and concentrated in vacuo to give 11.5 g of crude ketone. Purification on neutral alumina using ethyl acetate-cyclohexane (1:1) as eluant afforded the title compound (D6) as a colorless oil which solidified on cooling (7.0 g; 64%).

Description 7

(±) 5-Acetyl-1-azabicyclo[3.2.1]octane (D7)

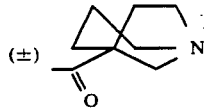

A solution of (±) ethyl 1-azabicyclo[3.2.1]oct-5-ylcarboxylate (D2, 6.0 g, 0.033 mole) in ethanol (20 ml) was treated with a solution of lithium hydroxide monohydrate (1.43 g, 0.034 mole) in water (60 ml). The mixture was stirred at room temperature for 18 h and then concentrated in vacuo to leave a white solid, which was dried thoroughly. A stirred suspension of this material (finely powdered) in dry THF (350 ml) under nitrogen was cooled to 0° C. and treated with methyllithium (30.0 ml of 1.4 M solution in ether, 0.042 mole). The reaction mixture was heated under reflux for 5.5 h and then cooled to room temperature before adding to excess cold dilute hydrochloric acid. The aqueous mixture was basified with potassium carbonate solution and extracted with chloroform (3×100 ml). The combined extracts were dried (Na2SO4) and concentrated in vacuo to leave a yellow oil, which was purified by passage through a basic alumina column eluting with ethyl acetate, to give the title compound (D7) as a pale yellow oil (2.35 g, 45%).

$^1$H Nmr (CDCl3) δ: 1.45–1.55 (1H, m), 1.65–1.90 (4H, m), 2.00–2.10 (1H, m), 2.15 (3H, s), 2.65–3.00 (5H, m), 3.05–3.20 (1H, m).

Ir (film) υ C=O 1695 cm$^{-1}$.

Description 8

(±)exo-Ethyl 1-azabicyclo[2.2.1]hept-3-ylcarboxylate (D8)

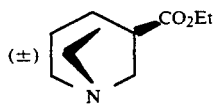

(±)exo-Ethyl 1-benzyl-1-azoniabicyclo[2.2.1]hept-3-ylcarboxylate bromide (EP A 0257741 Description 9) (54 g, 0.16 mole) was dissolved in ethanol (400 ml) and hydrogenated over 10% Pd-C (8.5 g) at atmospheric pressure and 25° C. After 2 h the solution was filtered and concentrated in vacuo to leave a gum. This was partitioned between chloroform and saturated aqueous potassium carbonate solution and the organic phase separated, dried (Na2SO4) and concentrated in vacuo to leave a gum. This gum was distilled to give the title compound (D8) as a colorless oil (23 g, 85%) b.p. 150° C. at 0.5 mmHg.

$^1$H Nmr (CDCl3) δ: 1.10–1.20 (1H,m), 1.25 (3H,t,J=7Hz), 1.54–1.67 (1H,m), 2.15–2.25 (1H,m), 2.28–2.35 (1H,m), 2.38–2.50 (1H,m), 2.60–2.67 (1H,m), 2.70–2.90 (3H,m), 2.93–3.03 (1H,m), 4.13 (2H,q,J=7Hz).

Description 9

(±) exo-1-Azabicyclo[2.2.1]hept-3-ylcarboxaldehyde (D9)

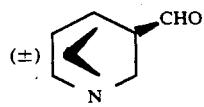

A stirred solution of (±) exo-ethyl 1-azabicyclo-[2.2.1] hept-3-ylcarboxylate (D8, 1.7 g, 0.010 mole) in dry toluene (50 ml) at −65° C. under nitrogen was treated with 1.5 M diisobutylaluminium hydride in toluene (9.2 ml, 0.014 mole) and stirred at −65° C. for 4 h. The solution was treated with glacial acetic acid (3 ml) and allowed to warm up to room temperature, then basified with 10% sodium hydroxide solution, saturated with potassium carbonate and extracted with chloroform (3×60 ml). The combined extracts were dried (Na2SO4) and concentrated in vacuo to give a colorless oil (1.0 g), which contained the title compound (D9). This was used without purification.

Description 10

(±) trans-3-Acetyl-1-azabicyclo[2.2.2]octane oxime (D10)

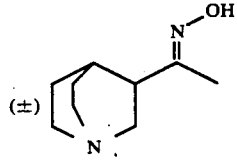

(±) 3-Acetyl-1-azabicyclo[2.2.2]octane (D6, 1.15 g, 0.0075 mole) in methanol (30 ml) was treated with hydroxylamine hydrochloride (0.53 g, 0.0076 mole) at room temperature for 17 h. The reaction mixture was concentrated in vacuo and the residue was recrystallized from methanol/acetone to give the hydrochloride salt of the oxime as a white crystalline solid (1.27 g). Water (30 ml) was added to the salt and the mixture was saturated with potassium carbonate and extracted with chloroform (5×40 ml). The combined organic extracts were dried (Na₂SO₄) and evaporated to yield the title compound (D10) as a white crystalline solid (0.97 g, 77%) m.p. 252° C. (dec.).

Description 11

(±) 1-Azabicyclo[3.2.1]oct-5-yl-N-methoxy-N-methyl-carboxamide (D11)

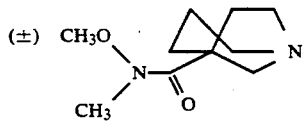

(D11)

(±) Ethyl-1-azabicyclo[3.2.1]oct-5-ylcarboxylate (D2, 5 g, 0.027 mole) in hydrochloric acid (5 N, 150 ml) was heated under reflux for 1.5 h. The reaction was then concentrated in vacuo to a hygroscopic solid which was dissolved in thionyl chloride (100 ml) and heated under reflux for 0.5 h. The mixture was then concentrated in vacuo to a gum, which was freed from excess thionyl chloride by co-evaporation with toluene. The residue was dissolved in absolute chloroform (100 ml) and treated with N,O-dimethylhydroxylamine hydrochloride (2.92 g, 0.030 mole). After cooling to 0° C. pyridine (10.9 ml, 0.135 mole) was added dropwise. The reaction was allowed to warm to room temperature and stirred for 1 h. The reaction mixture was poured into saturated aqueous potassium carbonate solution (100 ml) and the mixture was extracted with chloroform (4×100 ml). The combined organic extracts were dried (Na₂SO₄) and evaporated to give an oil which was distilled in vacuo to afford the title compound (D11) (3.77 g, 69%) b.p. 160° C. at 0.5 mmHg.

¹H-Nmr (CDCl₃) δ: 1.47 (1H, m), 1.68–2.13 (7H, m), 2.78–3.15 (6H, m), 3.17 (3H, s), 3.67 (3H, s).

Description 12

(±) 5-Propan-1-one-1-azabicyclo[3.2.1]octane (D12)

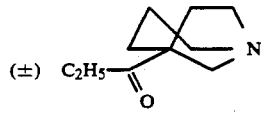

(D12)

Ethylmagnesium bromide (2.9 ml of a 3 M solution in ether, 0.0087 mole) was added dropwise to (±) 1-azabicyclo[3.2.1]oct-5-yl-N-methoxy-N-methyl-carboxamide (D11, 0.85 g, 0.0043 mole) in dry THF (50 ml) at 0° C. After 2 h at 0° C. the reaction was poured into ice-cold 2.5 M hydrochloride acid (50 ml). The mixture was made basic, then saturated, with potassium carbonate and extracted with chloroform (4×75 ml). The combined extracts were dried (Na₂SO₄) and evaporated to give the crude product (0.66 g) which was chromatographed on silica using 10% methanol/chloroform as eluant to yield the title compound (D12) as an oil (0.44 g, 61%).

¹H-Nmr (CDCl₃) δ: 1.05 (3H, t, J=7Hz), 1.50–1.67 (1H, m), 1.72–1.92 (4H, m), 2.05 (1H, m), 2.48 (2H, m, J=7Hz), 2.74–3.00 (5H, m), 3.13 (1H, m).

Description 13

(±) exo-1-Azabicyclo[2.2.1] hect-3-yl-N-methoxy-N-methylcarboxamide (D13)

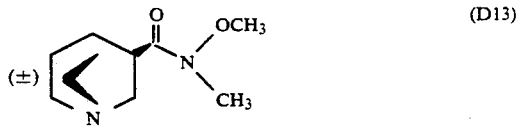

(±) exo-Ethyl-1-azabicyclo[2.2.1]hept-3-ylcarboxylate (D8) (8.0 g, 0.047 moles) in hydrochloric acid (5 N, 250 ml) was heated under reflux for 1.5 h. The reaction was then concentrated in vacuo to a solid which was dissolved in thionyl chloride (200 ml) and heated under reflux for 0.5 h when the copious evolution of sulphur dioxide and hydrogen chloride ceased. The reaction was then concentrated in vacuo to a gum, which was freed from excess thionyl chloride by co-evaporation with toluene. The residue was dissolved in dry acetonitrile (200 ml) under an atmosphere of nitrogen and treated with N,O-dimethylhydroxylamine hydrochloride (5 g, 0.05 mole). After cooling to 0° C. pyridine (18 g, 0.230 mole) was added dropwise. The reaction was allowed to warm to room temperature over a period of 16 h. The solvent was then removed in vacuo and the residue partitioned between saturated aqueous potassium carbonate solution and chloroform. The organic phase was separated, dried over sodium sulphate and concentrated in vacuo to a gum, which was distilled in vacuo to afford the title compound (D13) (3.1 g, 36%) b.p. 150° C. at 0.1 mmHg.

¹H Nmr (CDCl₃) δ: 1.2 and 1.6 (each 1H, m, 5—CH₂); 2.33 (1H, m, 4-H); 2.5 (2H, m); 2.7–3.0 (5H, m); 3.18 (3H, s, N-CH₃); 3.70 (3H, s, O-CH₃).

Description 14

(±) exo- and endo-3-Acetyl-1-azabicyclo2.2.1]heptane (D14)

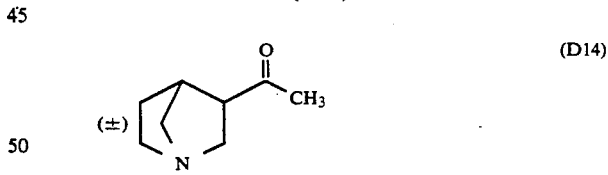

(D14)

A solution of (±) exo-1-azabicyclo[2.2.1]hept-3-yl-N-methyl-N-methoxy carboxamide (D13) (3.10 g, 0.168 mole) in dry tetrahydrofuran (65 ml) was cooled to 0° C. and treated with methyl lithium in hexane (11.1 ml, 1.6 M, 0.017 mole) under an atmosphere of nitrogen for 1.5 h. The reaction was then quenched by the addition of acetic acid (3 ml) and concentrated in vacuo. The resulting gum was then partitioned between saturated aqueous potassium carbonate solution and chloroform. The organic phase was separated, dried over sodium sulphate and concentrated in vacuo to a gum, which was distilled at 150° C. and 0.2 mmHg to afford the title compound (D14) (1.5 g, 65%) as 9:1 mixture of exo and endo isomers.

¹H Nmr (CDCl₃) (signals corresponding to major exo isomer) δ: 1.2 and 1.6 (each 1H, m, 5—CH₂); 2.18 (3H, s, CH₃); 2.2-2.9(6H, m, 3—C$\underline{H}$, 2—C$\underline{H}$, 6—C$\underline{H_2}$, 7—C$\underline{H_2}$); 3.0 (1H, d,d,d, J=12Hz, 6Hz, 3Hz, 2—C$\underline{H}$).

Description 15

(±) exo-3-Propan-1-one-1-azabicyclo[2.2.1]heptane (D15)

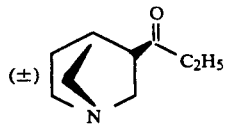
(D15)

(±) exo-1-Azabicyclo[2.2.1]hept-3-yl-N-methyl-N-methoxycarboxamide (D13, 0.5 g, 0.0027 mole) was treated with ethylmagnesium bromide (1.36 ml of a 3 M solution in ether, 0.0041 mole) in THF (25 ml) as in the method of Description 12 to yield the title compound (D15) as an oil (0.23 g, 54%).

¹H-Nmr'(CDCl₃) δ: 1.06 (3H, t, J=7Hz), 1.18 (1H, m), 1.62 (1H, m), 2.22-2.73 (8H, m), 2.83 (1H, m), 3.00 (1H, m).

¹³C-Nmr (CDCl₃) δ: 8.12, 30.54, 35.97, 41.13, 54.18, 54.20, 57.77, 58.60, 211.93.

Description 16

(±) Methyl 1-benzyl-2-oxo-4-pyrrolidylcarboxylate (D16)

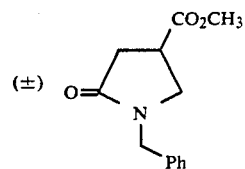
(D16)

A solution of dimethyl itaconate (50 g, 0.32 mole) in methanol (40 ml) was treated with benzylamine (34.6 ml, 0.32 mole) and the mixture heated under reflux for 2.5 h. The solution was then concentrated in vacuo and the residue purified by distillation (b.p. 162° C.-170° C./0.2 mmHg) to give a pale yellow oil. This solidified on standing to give the title compound (D16) as a beige solid (66.2 g, 89%), m.p. 62° C.-63° C.

Description 17

(±) Methyl 1-benzyl-3-pyrrolidylcarboxvlate (D17)

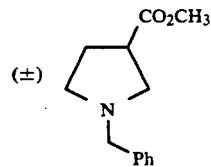
(D17)

A solution of (±) methyl 1-benzyl-2-oxo-4-pyrrolidylcarboxylate (D16, 35.4 g, 0.18 mole) in dry THF (135 ml) was added dropwise over 30 mins to 1 M borane-THF solution (228 ml, 0.23 mole) at 0° C. under nitrogen, and when addition was complete the solution was heated under reflux for 1 h. The solution was cooled to room temperature, then treated dropwise with 8% hydrogen chloride/methanol (114 ml, 0.25 mole HCl) and stirred for 18 h, followed by 3 h at reflux. The mixture was then concentrated in vacuo and the residue treated with water (40 ml), washed with ether (2×50 ml), basified with 40% sodium hydroxide solution, saturated with potassium carbonate and extracted with ether (3×70 ml). The combined extracts were dried (Na₂SO₄) and concentrated in vacuo to leave a yellow oil, which was purified by distillation (b.p. 146° C./0.7 mmHg) to give the title compound (D17) as a colorless oil (19.8 g, 50%).

Description 18

(±) 7-Benzyl-7-aza-2-oxaspiro[4.4]nonan-1-one (D18)

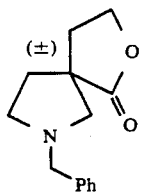
(D18)

A solution of diisopropylamine (6.6 ml, 0.047 mole) in dry ether (100 ml) at −65° C. under nitrogen was treated with 1.6 M n-butyllithium in hexane (26.2 ml, 0.042 mole) and the solution stirred for 15 min, before treating with N,N,N',N'-tetramethylethylenediamine (12.3 ml). After stirring for a further 10 min, the solution was treated dropwise over 10 min with a solution of (±) methyl 1-benzyl-4-pyrrolidylcarboxylate (D17, 7.50 g, 0.034 mole) in dry ether (20 ml) and stirring continued at −65° C. for 15 min. Ethylene oxide (3.1 g, 0.070 mole) was then bubbled into the solution over 20 min and the mixture was allowed to warm to room temperature over 2 h followed by 40 min at reflux. The reaction mixture was treated with saturated sodium hydrogen carbonate solution (50 ml) and extracted with ether (3×100 ml). The combined extracts were dried (Na₂SO₄) and concentrated in vacuo to leave an orange oil. The unreacted starting material was removed by heating under reflux in 8 M hydrochloric acid (50 ml) for 2 h, followed by basifying to saturation with sodium hydrogen carbonate and extraction with ether. The organic extract was dried (Na₂SO₄) and concentrated in vacuo to leave an orange oil, which was distilled in a Kugelröhr apparatus (b.p. 190° C.-210° C./0.2-0.5 mmHg) followed by column chromatography on silica gel eluting with ether, to give the title compound (D18) as a pale yellow oil (2.50 g, 36%).

Description 19

Ethyl 1-benzyl-1-azoniabicyclo[2.2.1] hept-4-yl-carboxylate bromide (D19)

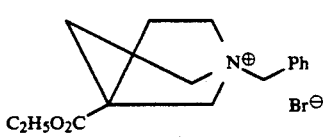
(D19)

(±) 7-Benzyl-7-aza-2-oxaspiro[4,4]nonan-1-one (D18, 2.5 g, 0.012 mole) was treated with a saturated solution of hydrogen bromide in ethanol (150 ml) and the resulting solution allowed to stand at room temperature for 3.5 days. The solution was concentrated in vacuo and the residue basified with saturated potassium carbonate solution, stirred for 10 mins and then extracted with chloroform (3×50 ml). The combined extracts were dried (Na₂SO₄) and concentrated in vacuo to give the title compound (D19) as a beige solid (3.40 g, 87%).

Description 20

Ethyl 1-azabicyclo[2.2.1]hept-4-ylcarboxylate (D20)

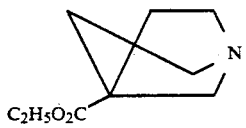

D(20)

Ethyl 1-benzyl-1-azoniabicyclo[2.2.1]hept-4-ylcarboxylate bromide (D19, 15 g, 0.044 mole) in ethanol (250 ml) was hydrogenated over 10% Pd on carbon (1 g). The reaction was then filtered through celite and the filtrate concentrated in vacuo to yield the crystalline hydrobromide. The salt was partitioned between chloroform and saturated aqueous potassium carbonate solution. The organic phase was separated, dried, concentrated in vacuo and distilled to give the title compound (D20) as a colorless oil (7.7 g, 68%), b.p. 203° C.-205° C. at 10 mmHg.

Description 21

1-Azabicyclo[2.2.1] hept-4-yl-N-methoxy-N-methyl carboxamide (D21)

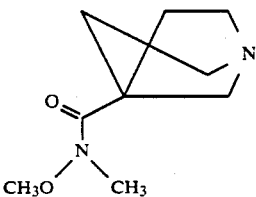

(D21)

Ethyl-1-azabicyclo[2.2.1]hept-4-ylcarboxylate (D20, 1.75 g, 0.01 mole) in concentrated hydrochloric acid (50 ml) was heated under reflux for 1.5 h. The reaction was then concentrated in vacuo to give a solid which was dissolved in thionyl chloride (30 ml) and heated under reflux for 1.5 h. The mixture was then evaporated to dryness, and freed from residual thionyl chloride by co-evaporation which toluene. The residue was then dissolved in dry acetonitrile (50 ml) and treated with N,O-dimethylhydroxylamine hydrochloride (0.73 g, 0.0075 mole) and triethylamine (4.5 ml, 0.032 mole). The mixture was stirred overnight at room temperature and then filtered to remove most of the triethylamine hydrochloride. The filtrate was evaporated to dryness and saturated potassium carbonate solution was added. The product was then extracted into chloroform (3×100 ml) and the combined extracts were dried (Na$_2$SO$_4$), filtered and evaporated to dryness to give the title compound (D21) as a white solid (0.79 g, 41%).

$^1$H-Nmr, 60 MHz (CDCl$_3$) δ: 1.6-2.1 (4H, m), 2.4-3.1 (6H, m), 3.15 (3H, s, N-Me), 3.62 (3H, s, N-OMe).

Description 22

1-Azabicyclo[2.2.1]hept-4-ylcarboxaldehyde (D22)

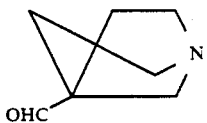

(D22)

1-Azabicyclo[2.2.1]hept-4-yl-N-methoxy-N-methyl-carboxamide (D21, 0.38 g, 0.0021 mole) was dissolved in dry toluene (20 ml) and cooled to −78° C. under a nitrogen atmosphere. Diisobutylaluminium hydride (1.5 M solution in toluene, 3.0 ml, 0.0045 mole) was added dropwise. The reaction was then allowed to warm to room temperature over a period of 2 h. Hydrochloric acid (2 N, 30 ml) was added rapidly with vigorous stirring. The aqueous layer was saturated with potassium carbonate and the mixture extracted with chloroform (3 ×100 ml). The combined extracts were dried (Na$_2$SO$_4$) and evaporated to dryness to yield the title compound (D22) (0.18 g, 70%). The aldehyde was used directly in any subsequent reactions without purification.

Description 23

4-Acetyl-1-azabicyclo[2.2.1]heptane (D23)

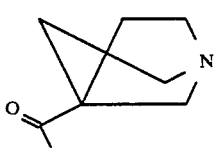

(D23)

1-Azabicyclo[2.2.1]hept-4-yl-N-methoxy-N-methyl-carboxamide (D21, 0.38 g, 0.0021 mole) was dissolved in dry tetrahydrofuran (20 ml) and cooled to 0° C. under a nitrogen atmosphere. Methyl lithium (1.3 ml of a 1.6 M solution in ether, 0.0021 mole) was added dropwise with stirring. The mixture was stirred at 0° C. for 1 h. A further amount of methyl lithium solution (0.3 ml, 0.0005 mole) was added and the mixture stirred for another 0.5 h. Glacial acetic acid (0.3 ml, 0.005 mole) was added and the mixture evaporated to dryness. The residue was partitioned between saturated potassium carbonate solution and chloroform. The organic layer was dried (Na$_2$SO$_4$) and evaporated to dryness to yield the title compound (D23) (0.3 g, 100%) which was used without further purification.

Description 24

(±)exo-3-Cyano-1-azabicyclo[3.2.1]octane (D24)

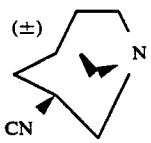

(D24)

1-Azabicyclo[3.2.1]octan-3-one* (2.7 g; 0.022 mole) in dry 1,2-dimethoxyethane (300 ml), under nitrogen, was treated with tosylmethyl isocyanide (3.5 g; 0.029 mole) and ethanol (4.6 ml) at 0° C. Potassium t-butoxide (6.8 g, 0.06 mole) was added portionwise at such a rate as to be able to maintain the temperature between 5° C.

and 10° C. The reaction mixture was allowed to warm to room temperature over 30 min, and then heated at 40° C. for a further 2.5 h. The mixture was cooled and filtered and the residue washed with 1,2-dimethoxyethane. The combined filtrates were concentrated in vacuo and the residual gum purified by column chromatography on alumina eluting with 20% methanol in ethyl acetate. The title (D24) compound was obtained as an oil (2.0 g; 66%).
*D. P. Thill and H. S. Aaron, J. Org. Chem., 1968, 33, 4376.

Ir υ (CN) 2225 cm$^{-1}$.

Description 25

(±)exo-1-Azabicyclo[3.2.1]oct-3-ylcarboxaldehyde (D25)

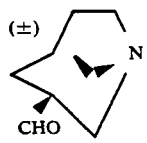

A suspension of potassium t-butoxide (1.95 g, 0.016 mole) in dry tetrahydrofuran (50 ml), cooled to −20° C. under nitrogen, was treated with methoxymethyl triphenylphosphonium chloride (5.49 g, 0.016 mole). The mixture was stirred at −20° C. for 30 min. To the resulting bright red solution was added dropwise a solution of 1-azabicyclo[3.2.1]octan-3-one* (1.0 g, 0.008 mole). After a further 1 h at −200° C. the reaction was quenched by the addition of 5N sulphur acid (15 ml). The aqueous layer was washed with chloroform (2×10 ml), then cooled in ice and treated dropwise with concentrated sulphur acid (3 ml). The solution was stirred at 0° C. for 30 min, then cooled to −78° C. and treated with potassium carbonate until saturation. After exhaustive extraction with chloroform (8×50 ml) the organic layers were dried (Na$_2$SO$_4$) and concentrated in vacuo to give the title compound (D25) as an oil (0.86 g, 76%) which was used immediately in the next stage without purification.
*D. P. Thill and H. S. Aaron, J. Org. Chem., 1968, 33, 4376.

Ir (film) 1715 cm$^{-1}$ ($\nu_{c=o}$)

$^1$H NMR (CDCl$_3$) δ: 1.55–2.05 (4H, m), 2.35 (1H, m), 2.50–3.10 (7H, m), 9.52 (1H, d, J=1Hz, CHO).

Description 26

(±)exo-3-Acetyl-1-azabicyclo[3.2.1]octane (D26)

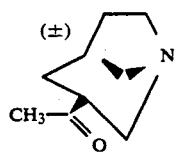

A solution of (±) exo-3-cyano-1-azabicyclo[3.2.1]-octane (D24) (1.10 g, 0.0081 mole) in dry ether (25 ml) cooled to −10° C. under nitrogen was treated dropwise with methyl lithium (7.1 ml of a 1.6 M solution in ether, 0.011 mole). The mixture was stirred at 0° C. for 2 h, then cooled to −78° C., and quenched rapidly with 5 N sulphur acid (20 ml). After adjusting the pH to 7–8 with potassium carbonate, the aqueous phase was washed with ether (2×100 ml). The aqueous layer was then saturated with potassium carbonate and extracted exhaustively with chloroform. Concentration of the dried (Na$_2$SO$_4$) extracts afforded a yellow oil (1.1 g) which was purified on neutral alumina using chloroform as eluant. Pooling of pure fractions afforded the title compound (D26) as a colorless oil (0.31 g, 23%). Earlier fractions afforded slightly less pure ketone (0.91 g, 68%).

Ir (film) 1700 cm$^{-1}$ ($\nu_{c=o}$).

$^1$H NMR (CDCl$_3$) δ: 1.60–1.80 (4H, m), 2.10 (3H, s, CH$_3$), 2.32 (1H, m), 2.58 (1H, m), 2.70–3.10 (6H, m).

EXAMPLE 1

(±) syn-1-Azabicyclo[3,2,1]oct-5-ylcarboxaldehyde, O-methyloxime hydrochloride salt (E1)

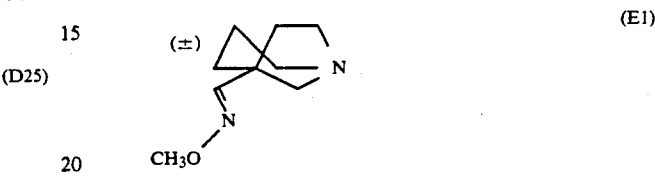

(±) 1-Azabicyclo[3.2.1]oct-5-ylcarboxaldehyde (D3, 3.61 g, assumed 0.0231 mole) in methanol (30 ml) was treated with methoxylamine hydrochloride (2.2 g, 0.0263 mole) at room temperature for 18 h. The reaction mixture was concentrated in vacuo, water (30 ml) was added and the mixture was saturated with potassium carbonate and extracted with chloroform (4×50 ml). The combined organic extracts were dried (Na$_2$SO$_4$) and evaporated to give an oil which was chromatographed on silica gel using 10% methanol/chloroform as eluant to yield the syn-oxime (2.81 g) as a single isomer. This material was converted to the hydrochloride and recrystallized from methanol/acetone to give the title compound (E1) as a white crystalline solid (2.69 g, 57%)

m.p. 190° C.–191° C.

Hydrochloride: $^1$H NMR (d$^6$-DMSO) δ: 1.62–2.17 (6H, m), 3.10–3.48 (6H, m), 3.75 (3H, s), 7.54 (1H, s).

$^{13}$C NMR (d$^6$ DMSO) δ: 16.49, 30.59, 31.06, 44.09, 49.55, 51.26, 58.59, 61.15, 151.49.

Free base: Ir (film) 1450, 1040cm$^{-1}$.

Analysis: C$_9$H$_{16}$N$_2$O.HCl requires C: 52.81, H: 8.37, N: 13.69; found C: 52.79, H: 8.21, N: 13.64.

EXAMPLE 2

(±) 1-Azabicyclo[2.2.2]oct-3-ylcarboxaldehyde, O-methyloxime hydrochloride salt (E2)

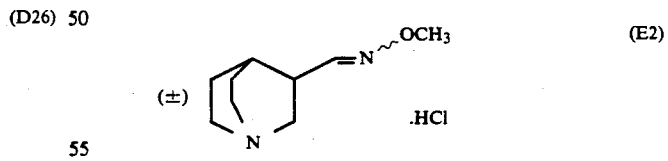

Crude (±) 1-azabicyclo[2.2.2]oct-3-ylcarboxaldehyde (comprising of approximately 50% aldehyde, D5, 1.9 g, assumed 0.0058 mole) in methanol (20 ml) was treated with methoxylamine hydrochloride (0.58 g, 0.0069 mole) as in the method of Example 1 to give the oxime (0.55 g) as a pale yellow oil. This material was converted to the hydrochloride to yield the title compound (E2) as a 3:2 mixture of syn and anti isomers (0.54 g, 46%) m.p. 162.5° C.–164° C.

Hydrochloride: $^1$H NMR (d$^6$-DMSO) δ: 1.64–1.96 (4H, m), 2.14 (1H, m), 2.86–3.51 (7H, m), 3.78 and 3.82 (3H, s), 7.06 and 7.58 (1H, d, J=6Hz).

Analysis: $C_9H_{16}N_2O \cdot HCl$ requires C: 52.81, H: 8.37, N: 13.69; found C: 52.52, H: 8.27, N: 13.48.

EXAMPLE 3

(±) trans-3-Acetyl-1-azabicyclo[2.2.2]octane-O-methyloxime hydrochloride salt (E3)

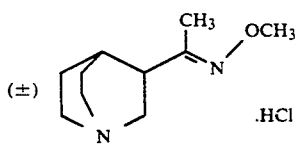
(E3)

(±) 3-Acetyl-1-azabicyclo[2.2.2]octane (D6, 1.17 g, 0.0076 mole) in methanol (10 ml) was treated with methoxylamine hydrochloride (0.64 g, 0.0077 mole) as in the method of Example 1 to give the trans-ketoxime (1.12 g) as a single isomer. This material was converted to the hydrochloride and recrystallized from methanol/acetone to yield the title compound (E3) as a white crystalline solid (1.03 g, 62%) m.p. 182° C.-183.5° C.

Hydrochloride: $^1$H NMR (d$^6$-DMSO) δ: 1.65 (2H, m), 1.80 (3H, s), 1.90 (2H, m), 2.26 (1H, m), 2.87 (1H, t, J=8Hz), 3.00-3.38 (5H, m), 3.54 (1H, dd, J=6 and 12Hz).

$^{13}$C NMR (d$^6$-DMSO) δ: 13.98, 18.18, 22.28, 22.96, 40.42, 45.13, 45.23, 46.02, 61.27, 154.94.

Free base: Ir (film) 1450, 1045cm$^{-1}$.

EXAMPLE 4

(±) syn-1-Azabicyclo[3.2.1]oct-5-ylcarboxaldehyde, O-proparqyloxime hydrochloride salt (E4)

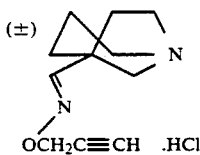
(E4)

(±) 1-Azabicyclo[3.2.1]oct-5-ylcarboxaldehyde (D3, 1.5 g, assumed 0.0096 mole) in methanol (15 ml) was treated with O-propargyl hydroxylamine hydrochloride (1.16 g, 0.0108 mole) (U.S. Pat. No. 3,398,180; CA: 57:72886b) at room temperature for 16 h. The reaction mixture was worked-up as in the method of Example 1 to yield the syn-oxime (1.35 g) which was converted to the hydrochloride and recrystallized from methanol/acetone to give the title compound (E4) as a white crystalline solid (1.23 g, 56%) m.p. 165° C.-166° C.

Hydrochloride: $^1$NMR (d$^6$-DMSO) δ: 1.62-2.18 (6H, m), 3.10-3.48 (6H, m), 3.50 (1H, t, J=1.5Hz), 4.63 (2H, d, J=1.5Hz), 7.62 (1H, s).

$^{13}$C NMR (d$^6$-DMSO) δ: 16.49, 30.61, 31.02, 44.25, 49.55, 51.24, 58.55, 60.97, 77.56, 79.93, 152.94.

Free base: Ir (film) 3280, 2100, 1450 cm$^{-1}$.

Analysis: $C_{11}H_{16}N_2O \cdot HCl$ requires C: 57.76, H: 7.49, N: 12.25;

Found C: 57.52; H: 7.16; N: 12.11.

EXAMPLE 5

(±) syn-1-Azabicyclo[3.2.1]oct-5-ylcarboxaldehyde, O-ethyloxime hydrochloride salt (E5)

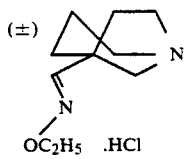
(E5)

(±) 1-Azabicyclo[3.2.1]oct-5-ylcarboxaldehyde (D3, 1.5 g, assumed 0.0096 mole) in methanol (15 ml) was treated with O-ethylhydroxylamine hydrochloride (1.05 g, 0.0108 mole) as in the method of Example 1 to afford the syn-oxime (1.17 g) as a single isomer. This material was converted to the hydrochloride and recrystallized from methanol/acetone to yield the title compound (E5) as a white crystalline solid (0.96 g, 46%) m.p. 162° C.-163° C.

Hydrochloride: $^1$NMR (d$^6$-DMSO) δ: 1.17 (3H, t, J=7Hz), 1.62-2.17 (6H, m), 3.10-3.50 (6H, m), 4.01 (2H, q, J=7Hz), 7.53 (1H, s).

$^{13}$C NMR (d$^6$-DMSO) δ: 14.28, 16.52, 30.66, 31.14, 44.19, 49.59, 51.30, 58.66, 68.63, 151.14.

Free base: Ir (film) 1450, 1045 cm$^{-1}$.

Analysis: $C_{10}H_{19}N_2O \cdot HCl$ requires C: 54.91; H: 8.76; N: 12.81;

Found C: 54.93; H: 8.74; N: 12.53.

EXAMPLE 6

(±) trans-5-Acetyl-1-azabicyclo[3.2.1]octane-O-methyloxime hydrochloride salt (E6)

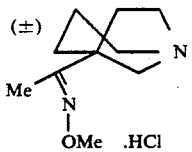
(E6)

(±) 5-Acetyl-1-azabicyclo[3.2.1]octane (D9, 0.48 g, 0.0031 mole) in methanol (10 ml) was treated with methoxylamine hydrochloride (0.26 g, 0.0031 mole) at room temperature for 16 h. The reaction mixture was concentrated in vacuo to give the crude product which was recrystallized from acetone/ether to yield the title compound (E6) as a white crystalline solid (0.51 g, 74%) m.p. 172° C.-173° C.

Hydrochloride: $^1$H NMR (d$_6$-DMSO) δ: 1.50-1.64 (1H,m), 1.74-2.15 (5H,m), 1.80 (3H,s), 3.15-3.50 (6H,m), 3.77 (3H,s).

$^{13}$C NMR (d$_6$-DMSO) δ: 11.37, 16.73, 29.92, 32.04, 47.85, 49.26, 51.12, 58.11, 58.28, 61.08, 157.88.

EXAMPLE 7

(±) exo-1-Azabicyclo[2.2.1]hept-3-ylcarboxaldehyde, O-methyloxime oxalate salt (E7)

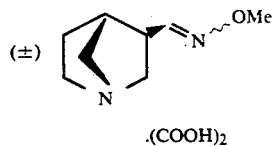

(±) exo-1-Azabicyclo[2.2.1]hept-5-ylcarboxaldehyde (D9, 1.1 g) in methanol (15 ml) was treated with methoxylamine hydrochloride (0.49 g, 0.0059 mole) as in the method of Example 1 to give the oxime (0.42 g) as a pale yellow oil. This material was converted to the oxalate and recrystallized from methanol/acetone to yield the title compound (E7) as a 7:1 mixture of syn and anti isomers (0.53 g, 37% from (D10) m.p. 133° C.-135° C.

Oxalate salt: $^1$H NMR (d$_6$-DMSO) δ: 1.68 (1H,m), 1.99 (1H,m), 2.74-2.90 (2H,m), 3.00-3.42 (6H,m), 3.76 (syn-isomer) and 3.82 (anti-isomer) (3H,s), 6.95 (anti-isomer) and 7.54 (syn-isomer) (1H,d,J=6Hz).

Free base: Ir (film) 1450, 1060, 1040 cm$^{-1}$.

Analysis: $C_8H_{14}N_2O \cdot C_2H_2O_4$ requires C: 49.18, H: 6.60, N: 11.47; found C: 49.21, H: 6.75, N: 11.44.

EXAMPLE 8

(±) exo-1-Azabicyclo[2.2.1]hept-3-ylcarboxaldehyde, O-ethyloxime oxalate salt (E8)

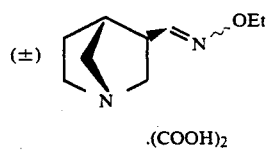

(±) exo-1-Azabicyclo[2.2.1]hept-5-ylcarboxaldehyde (D9, 1.0 g) in methanol (10 ml) was treated with O-ethylhydroxylamine hydrochloride (0.58 g, 0.0059 mole) according to the method described in Example 1 to give the oxime (0.50 g) as a yellow oil. This material was converted to the oxalate and recrystallized from methanol/acetone to yield the title compound (E8) as a 13:1 mixture of syn and anti isomers (0.44 g, 31% from (D10) m.p. 102° C.-104° C.

Oxalate salt: $^1$H NMR (d$_6$-DMSO) δ: 1.18 (3H,t,J=7Hz), 1.69 (1H,m), 1.99 (1H,m), 2.75-2.88 (2H,m), 3.02-3.40 (6H,m), 4.02 (2H,q,J=7Hz), 6.94 (anti-isomer) and 7.53 (syn-isomer) (1H,d,J=6Hz).

Free base: Ir (film) 1455, 1050 cm$^{-1}$.

Analysis $C_9H_{16}N_2O \cdot C_2H_2O_4$ requires C: 51.16, H: 7.03, N: 10.85; found C: 51.17, H: 7.22, N: 10.84.

EXAMPLE 9

(±) exo-1-Azabicyclo[2.2.1]hept-3-ylcarboxaldehyde, O-proparqyloxime oxalate salt (E9)

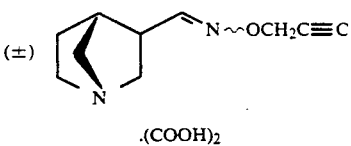

(±) exo-1-Azabicyclo[2.2.1]hept-5-ylcarboxaldehyde (D9, 1.0 g) in methanol (10 ml) was treated with O-propargylhydroxylamine hydrochloride (0.64 g, 0.0059 mole) according to the method described in Example 1 to give the oxime (0.61 g) as a yellow oil. This material was converted to the oxalate to yield the title compound (E9) as a 9:1 mixture of syn and anti isomers (0.57 g, 39% from (D10) m.p. 118° C.-121° C.

Oxalate salt: 1H NMR (d$_6$-DMSO) δ: 1.68 (1H,m), 1.99 (1H,m), 2.75-2.90 (2H,m), 3.00-3.55 (7H,m), 4.63 (syn-isomer) and 4.73 (anti-isomer) (2H,d,J=1.5Hz), 7.06 (anti-isomer) and 7.62 (syn-isomer) (1H,d,J=6Hz).

Free base: Ir (film) 3280, 2100, 1450, 1000 cm$^{-1}$.

EXAMPLE 10

(±) syn-1-Azabicyclo[3.2.1]oct-5-ylcarboxaldehyde-N,N-dimethylhydrazone oxalate salt (E10)

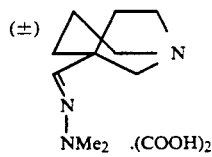

(±) 1-Azabicyclo[3.2.1]oct-5-ylcarboxaldehyde (D3, 2.43 g, assumed 0.0155 mole) in methanol (20 ml) was treated with dimethylhydrazine (1.30 ml, 0.0171 mole). Glacial acetic acid was added dropwise to give pH 4 (0.5 ml) and the mixture was stirred overnight. The reaction mixture was concentrated in vacuo, water (20 ml) was added and the mixture was saturated with potassium carbonate and extracted with chloroform (5×50 ml). The combined organic extracts were dried (Na$_2$SO$_4$) and evaporated to give an oil which was chromatographed on basic alumina using 2% methanol-/ethyl acetate as eluant to yield the syn-hydrazone (1.66 g, 59%) as a single isomer. A portion of this material was converted to the oxalate to yield the title compound (E10) as a white crystalline solid m.p. 125° C.-127° C.

Oxalate salt: $^1$NMR (d$_6$-DMSO) δ: 1.64-2.10 (6H,m), 2.68 (6H,s), 3.06-3.56 (6H,m), 6.59 (1H,s).

$^{13}$C NMR (d$_6$-DMSO) δ: 16.86, 31.62, 32.34, 42.58, 45.57, 49.71, 51.49, 59.72, 136.40.

Free base: Ir (film) 1450, 1220, 1000 cm$^{-1}$.

Analysis: $C_9H_{19}N_3 \cdot C_2H_2O_4$ requires C: 53.12, H: 7.8, N: 15.49; found C: 53.37, H: 7.97, N: 15.46.

EXAMPLE 11

(±) trans-3-Acetyl-1-azabicyclo[2.2.2]octane-O-acetyloxime oxalate salt (E11)

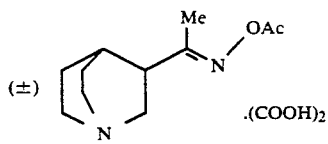

A mixture of (±) trans-3-acetyl-1-azabicyclo[2.2.2]octane oxime (D10, 0.26 g, 0.0017 mole) and triethylamine (0.24 ml, 0.0017 mole) in dichloromethane (10 ml) was cooled in an ice bath. Acetyl chloride (0.13 ml, 0.0018 mole) was added dropwise and the mixture was warmed to room temperature and stirred for 1 h. Water (20 ml) was added and the mixture was saturated with potassium carbonate and extracted with chloroform (4×ml). The combined organic extracts were dried ($Na_2SO_4$) and evaporated to give an oil which was chromatographed on silica gel using 10% methanol/chloroform as eluant to yield the trans-acetyloxime (0.26 g) as an oil. This material was converted to the oxalate which was triturated with acetone to yield the title compound (E11) as a white crystalline solid (0.32 g, 64%) m.p. 110° C.–112° C.

Oxalate salt: $^1$NMR ($d_6$-DMSO) δ: 1.70 (2H,m), 1.94 (2H,m), 1.99 (3H,s), 2.17 (3H,s), 2.20 (1H,m), 2.34 (1H,m), 3.00–3.40 (5H,m), 3.62 (1H,m).

$^{13}$C NMR ($d_6$-DMSO) δ: 15.37, 18.28, 22.34, 23.04, 39.64, 45.24 (x2), 46.11, 163.66, 168.29.

Free base: Ir (film) 1760, 1450, 1200 cm$^{-1}$.

EXAMPLE 12

(±)5-Propan-1-one-1-azabicyclo[3.2.1]octane-trans-O-methyloxime hydrochloride salt (E12)

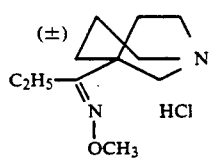

(±) 5-Propan-1-one-1-azabicyclo[3.2.1]octane (D12, 0.403 g, 0.0024 mole) in methanol (10ml) was treated with methoxylamine hydrochloride (0.21 g, 0.0024 mole) as in the method of Example 6 to give the crude product which was recrystallized from methanol/acetone to yield the title compound (E12) as a white crystalline solid (0.363 g, 59%) m.p. 153° C.–155° C.

Hydrochloride: $^1$H-Nmr ($d_6$-DMSO) δ: 1.03 (3H, t, J=7Hz), 1.50–1.66 (1H, m), 1.75–2.35 (7H, m), 3.10–3.52 (6H, m), 3.76 (3H, s).

$^{13}$C Nmr ($d_6$-DMSO) δ: 10.90,. 16.70, 19.65, 29.80, 31.97, 48.00, 49.34, 51.03, 58.29, 61.21, 162.04.

M.S. Calculated mass for $C_{11}H_{20}N_2O$=196.1576 Observed mass=196.1577.

EXAMPLE 13

(±)exo-3-Acetyl-1-azabicyclo[2.2.1]heptane-trans-O-methyloxime oxalate salt (E13)

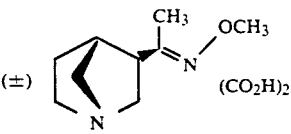

(±) 3-Acetyl-1-azabicyclo[2.2.1]heptane (D14, 0.23 g, 0.0012 mole) in methanol (10 ml) was treated with methoxylamine hydrochloride (0.104 g, 0.0013 mole) as in the method of Example 1 to give the oxime (0.26 g, 94%) as a pale yellow oil. A portion of this material was converted to the oxalate, trituration of the resultant gum with 1:1 ether/acetone gave the title compound (E13) as a single isomer (0.2 g) m.p. 103° C.–105° C.

Oxalate: $^1$H Nmr ($d_6$-DMSO) δ: 1.70 (1H, m), 1.84 (3H, s), 2.02 (1H, m), 2.76 (1H, m), 2.92–3.35 (6H, m), 3.58 (1H, m), 3.77 (3H, s).

$^{13}$C Nmr ($d_6$-DMSO) δ: 14.62, 27.02, 38.58, 45.27, 51.37, 53.11, 55.90, 61 24, 155.08.

M.S. Calculated mass for $C_9H_{16}N_2O$=168.1263 Observed mass=168.1271.

EXAMPLE 14

(±)exo-3-Acetyl-1-azabicyclo[2.2.1]heptane-trans-O-ethyloxime hydrochloride salt (E14)

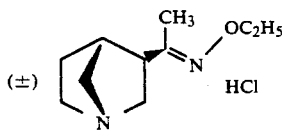

(±) 3-Acetyl-1-azabicyclo[2.2.1]heptane (D14, 0.48 g, 0.0035 mole) in methanol (10 ml) was treated with O-ethylhydroxylamine hydrochloride (0.34 g, 0.0035 mole) as in the method of Example 6 to give the crude oxime which was recrystallized from acetone/ether to yield the title compound (E14).as a white crystalline solid (0.59 g, 74%) m.p. 135° C.–136° C.

Hydrochloride: $^1$H-Nmr ($d_6$-DMSO) δ: 1.28 (3H, t, J=7Hz), 1.70 (1H, m), 1.95 (3H, s), 2.02 (1H, m), 2.78 (1H, m), 2.95–3.38 (6H, m), 3.60 (1H, m), 4.05 (2H, q, J=7Hz).

$^{13}$C Nmr ($d_6$-DMSO) δ: 14.51, 14.71, 26.84, 38.67, 45.25, 51.14, 52.79, 55.72, 68.58, 154.53.

M.S. Calculated mass for $C_{10}H_{18}N_2O$=182.1419 Observed mass=182.1410.

EXAMPLE 15

(±)exo-3-Acetyl-1-azabicyclo2.2.1]heptane-trans-O-proparqyloxime hydrochloride salt (E15)

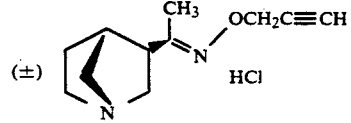

(±) 3-Acetyl-1-azabicyclo[2.2.1]heptane (D14, 0.40 g, 0.0029 mole) was treated with O-propargylhydroxylamine hydrochloride (0.31 g, 0.0029 mole) as in the method of Example 6 to give the crude product which was recrystallized from methanol/acetone to yield the title compound (E15) as a white crystalline solid (0.56 g, 85%) m.p. 191° C.-192° C.

Hydrochloride: $^1$H Nmr (d$_6$-DMSO) δ: 1.70 (1H, m), 1.87 (3H, s), 2.03 (1H, m), 2.83 (1H, m), 2.90-3.38 (6H, m), 3.47 (1H, m), 3.58 (1H, m), 4.67 (2H, m).

$^{13}$C Nmr (d$_6$-DMSO) δ: 14.79, 26.80, 38.71, 45.27, 51.18, 52.82, 55.70, 60.95, 77.29, 80.29, 156.46.

M.S. Calculated mass for $C_{11}H_{16}N_2O$ = 192.1263 Observed mass = 192.1256.

EXAMPLE 16

(±)exo-3-Propan-1-one-1-azabicyclo2.2.1 1heptane-trans-O-methyloxime hydrochloride salt (E16)

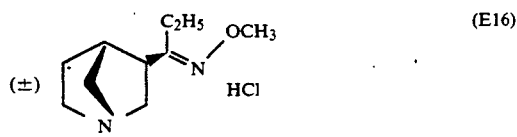

(±) exo-3-Propan-1-one-1-azabicyclo[2.2.1]heptane (D15, 0.20 g, 0.0013 mole) in methanol (5 ml) was treated with methoxylamine hydrochloride (0.11 g, 0.0013 mole) as in the method of Example 1 to give the oxime as a pale yellow oil (0.22 g, 92%). A portion of this material was converted to the hydrochloride and recrystallized from methanol/acetone to yield the title compound (E16) as a hygroscopic crystalline solid m.p. 119° C.-121° C.

Hydrochloride: $^1$H Nmr (d$_6$-DMSO) δ: 1.01 (3H, t, J=7Hz), 1.70 (1H, m), 2.02 (1H, m), 2.12-2.45 (2H, m), 2.83-3.62 (8H, m), 3.78 (3H, s).

$^{13}$C Nmr (d$_6$-DMSO) δ: 0.32, 21.98, 27.21, 39.21, 43.33, 51.45, 53.55, 56.09, 61.67, 159.69.

Free base: Ir (film) 1450, 1260, 1045 cm$^{-1}$.

EXAMPLE 17

(±)1-Azabicyclo[2.2.2]oct-3-ylcarboxaldehyde, O-proparqyloxime hydrochloride salt (E17)

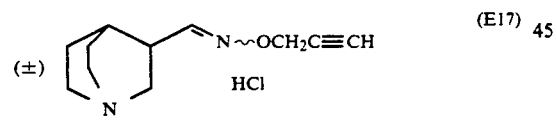

Crude (±) 1-azabicyclo[2.2.2]oct-3-ylcarboxaldehyde (comprising of approximately 50% aldehyde, D5, 4.24 g, assumed 0.0129 mole) in methanol (30 ml) was treated with O-propargylhydroxylamine hydrochloride (2.0 g, 0.0186 mole) as in the method of Example 1 to give the required oxime (2.7 g, 90%) as a 2:1 mixture of syn and anti isomers. This material was converted to the hydrochloride and repeatedly recrystallized from methanol/acetone to yield the title compound (E17) as a 9:1 mixture of syn and anti isomers m.p. 148° C.-150° C.

Hydrochloride: $^1$H Nmr (d$_6$-DMSO) δ: 1.64-1.97 (4H, m), 2.15 (1H, m), 2.89-3.46 (7H, m), 3.40 (1H, m), 4.66 (2H, m), 7.17 (syn) and 7.64 (anti) (1H, d, J=5Hz).

$^{13}$C Nmr (d$_6$-DMSO) Major isomer δ: 18.32, 22.81, 23.37, 33.75, 44.95, 45.21, 46.75, 60.88, 77.44, 80.05, 151.91.

Analysis: $C_{11}H_{16}N_2O$·HCl requires C: 57.76, H: 7.49, N: 12.24; found: C: 57.57, H: 7.46, N: 12.21.

EXAMPLE 18

(±) exo-1-Azabicyclo[2.2.1]hept-3-ylcarboxaldehyde-syn-dimethylhydrazone dioxalate salt (E18)

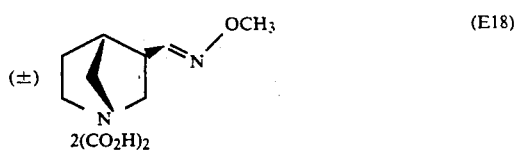

(±) exo-1-azabicyclo[2.2.1]hept-3-ylcarboxaldehyde (D9, 0.44 g, 0.0035 mole) was dissolved in ethanol (20 ml) and 1,1 dimethylhydrazine (0.3 ml, 0.0039 mole) was added followed by glacial acetic acid (3 drops). The mixture was stirred overnight at room temperature and then evaporated to dryness. The residue was partitioned between saturated potassium carbonate solution and chloroform. The organic layer was dried (Na$_2$SO$_4$) and evaporated to dryness. The residue was subjected to column chromatography on alumina (30 g) eluting with chloroform. This gave a pale yellow oil (0.15 g). Treatment with anhydrous oxalic acid gave the title compound (E18) (0.077 g, 6%) m.p. 103° C.-106° C.

Dioxalate salt: $^1$H Nmr (d$_6$-DMSO) δ: 1.6-1.77 (1H, m), 1.91-2.08 (1H, m), 2.71 (6H, s), 2.72-2.82 (2H, m), 3.02-3.55 (6H, m), 7.62 (1H, d), 10.40-11.50 (4H, brs).

$^{13}$C Nmr (D$_6$-DMSO) δ: 26.76, 40.42, 42.29, 42.74, 51.48, 54.66, 56.01, 134.94, 163.07.

Analysis: $C_{13}H_{21}N_3O_8$ requires C: 44.96, H: 6.05, N: 12.10; found C: 44.61, H: 5.66, N: 11.94.

EXAMPLE 19 syn-1-Azabicyclo[2.2.1]hept-4-ylcarboxaldehyde, O-methyloxime hydrochloride salt (E19)

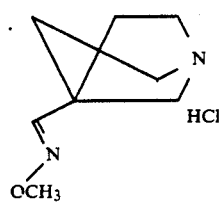

1-Azabicyclo[2.2.1]hept-4-ylcarboxaldehyde (D22, 0.45 g, 0.0036 ml) was dissolved in ethanol (20 ml) and methoxylamine hydrochloride (0.35 g, 0.0042 mole) was added. The mixture was heated on a steam bath for 1h and then allowed to cool. The mixture was then evaporated to dryness and the residue partitioned between saturated potassium carbonate solution and chloroform. The organic layer was dried (Na$_2$SO$_4$), evaporated to dryness and subjected to column chromatography on alumina eluting with chloroform. This gave an oil which was converted to the hydrochloride to give the title compound (E19) (0.11 g, 11%) m.p. 189° C.-193° C.

Hydrochloride salt: $^1$H Nmr (d$_6$-DMSO) δ: 1.82-2.03 (2H, m), 2.19-2.33 (2H, m), 3.33 (2H, s), 3.35-3.62 (4H, m), 3.91 (3H, s), 7.86 (1H, s), 11.35-11.50 (1H, brs).

$^{13}$C Nmr (d$_6$-DMSO) δ: 30.36, 47.74, 51.94, 59.68, 61.25, 148.07.

Analysis: $C_8H_{15}N_2OCl$ requires C: 50.39, H: 7.93, N: 14.69; found C: 49.16, H: 7.81, N: 14.28.

EXAMPLE 20

4-Acetyl-1-azabicyclo[2.2.1]heptane-O-methyloxime oxalate salt (E20)

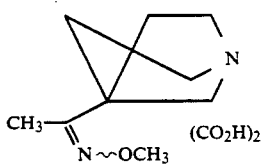
(E20)

4-Acetyl-1-azabicyclo[2.2.1]heptane (D23, 0.3 g, 0.0021 mole) was dissolved in ethanol (10 ml) and methoxylamine hydrochloride (0.27 g, 0.0032 mole) added. The mixture was stirred at room temperature for 24 h and then evaporated to dryness. The residue was partitioned between saturated potassium carbonate solution and chloroform. The organic layer was dried ($Na_2SO_4$) and evaporated to dryness. The residue was subjected to column chromatography on alumina (20 g) eluting with chloroform. This gave a colorless oil (0.35 g). Treatment with anhydrous oxalic acid gave the title compound (E20) as a 4:1 mixture of trans and cis isomers (0.33 g, 59%) m.p. 124° C.-6° C.

Oxalate salt: $^1$H Nmr ($d_6$-DMSO) δ: 1.95 (3H, s), 1.95-2.02 (1H, m), 2.05-2.18 (2H, m), 3.22 (cis) and 3.29 (trans) (2H, s), 3.29-3.40 (2H, m), 3.45-3.58 (2H, m), 3.79 (cis) and 3.87 (trans) (3H, s).

$^{13}$C Nmr ($d_6$-DMSO) δ: 12.10, 30.13 (cis) and 30.82 (trans), 51.77, 52.12, 59.37 (trans) and 59.70 (cis), 61.15 (trans) and 61.40 (cis), 154.88, 164.79.

Analysis: $C_{11}H_{18}N_2O_5$ requires C: 51.16, H: 7.03, N: 10.85; found: C: 50.94, H: 6.58, N: 10.80.

EXAMPLE 21 syn-1-Azabicyclo[2.2.1]hect-4-ylcarboxaldehyde, O-proparqyloxime oxalate salt (E21)

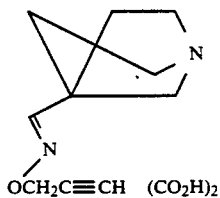
(E21)

1-Azabicyclo[2.2.1]hept-4-ylcarboxaldehyde (D22, 0.18 g, 0.0014 mole) was dissolved in ethanol (20 ml) and propargyloxime hydrochloride (0.25 g, 0.0023 mole) was added. The mixture was stirred at room temperature for 48 h and then evaporated to dryness. The residue was partitioned between saturated potassium carbonate solution and chloroform. The organic layer was dried ($Na_2SO_4$), evaporated to dryness and subjected to column chromatography on alumina (10 g) eluting with chloroform. This gave an oil which was treated with anhydrous oxalic acid to give the title compound (E21) (0.21 g, 54%) m.p. 153° C.-155° C.

Oxalate salt: $^1$H Nmr ($d_6$-DMSO) δ: 1.80-1.97 (2H, m), 2.13-2.29 (2H, m), 3.28 (2H, s), 3.29-3.40 (2H, m), 3.45-3.56 (2H, m), 3.60 (1H, s), 4.78 (2H, s), 7.90 (1H, s), 10.40-11.20 (2H, brs).

$^{13}$C Nmr ($d_6$-DMSO) δ: 30.61, 47.96, 52.11, 59.96, 61.02, 77.60, 79.95, 149.84, 164.70.

Analysis: $C_{12}H_{16}N_2O_5$ requires C: 53.73, H: 6.01, N: 10.44; found C: 53.75, H: 5.71, N: 10.36.

EXAMPLE 22

(±)exo-1-Azabicyclo2.2.1]hept-3-ylcarboxaldehyde, O-allyloxime oxalate salt (E22)

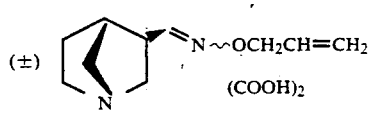
(E22)

(±)exo-1-Azabicyclo[2.2.1]hept-3-ylcarboxaldehyde (D9, 0.2 g) in ethanol (5 ml) was treated with O-allylhydroxylamine hydrochloride* (0.2 g, 0.0019 mole) at 70° C. for 1.5 h. The reaction mixture was worked-up as in the method of Example 1 to yield a 3:1 mixture of the syn and anti oximes (0.08 g, 28%). This material was converted to the oxalate salt and recrystallized from acetone/ether to yield the title compound (E22)

*E. Grochowski and J. Jurczak, Synthesis, 1976, 682. m.p. 80° C.-84° C.

Free base: $^1$H NMR (CDCl$_3$) δ: 1.15-1.30 (1H, m), 1.5-1.7 (1H, m), 2.18-2.95 (8H, m), 4.46-4.61 (2H, m), 5.15-5.35 (2H, m), 5.88-6.07. (1H, m), 6.58 (anti-isomer) and 7.32 (syn-isomer) (1H, d, J=6Hz).

EXAMPLE 23

(±)exo-1-Azabicyclo[3.2.1]oct-3-ylcarboxaldehyde, O-methyloxime hydrochloride salt (E23)

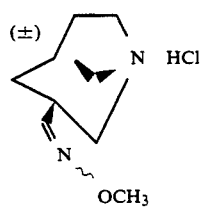
(E23)

A solution of (±) exo-1-azabicyclo[3.2.1]oct-3-ylcarboxaldehyde (D25, 0.43 g, 0.0031 mole) in methanol (25 ml) was treated with methoxyamine hydrochloride (0.28 g, 0.0034 mole) according to the method of Example 1. After chromatography on silica gel using 10% methanol/chloroform as eluant the product was converted into the hydrochloride salt. Crystallization from methanol/ether afforded the title compound (E23) (0.14 g, 25%) as a 95:5 mixture of syn and anti isomers, m.p. 194.5° C.-195° C. (dec).

Hydrochloride: $^1$H NMR ($d_6$-DMSO) δ: 1.70 (1H, m), 1.80-2.00 (2H, m), 2.18 (1H, m), 2.70 (1H, m), 2.95-3.60 (7H, m), 3.82 (syn-isomer) and 3.90 (anti-isomer) (3H, s), 6.75 (anti-isomer) and 7.44 (syn-isomer) (1H, d, J=7Hz).

$^{13}$C NMR ($d_6$-DMSO) Major isomer δ: 26.65, 29.19, 32.27, 32.66, 49.81, 52.97, 57.10, 61.06, 149.99.

EXAMPLE 24

(±)exo-3-Acetyl-1-azabicyclo[3.2.1]octane-trans-O-methyloxime hydrochloride salt

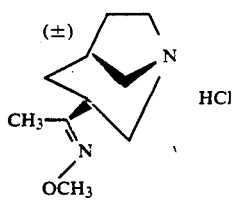
(E24)

A solution of (±)-exo-3-acetyl-1-azabicyclo[3.2.1]-octane (D26) (0.31 g, 0.002 mole) in methanol (20 ml) was treated with methoxylamine hydrochloride (0.19 g, 0.0022 mole) and stirred at room temperature for 2 days. The reaction mixture was worked up according to the method of Example 1 to give a yellow oil (0.19 g) which was converted into the hydrochloride salt. Recrystallization from methanol/ether afforded the title compound (E24) as colorless needles (0.09 g, 25%), m.p. 181° C.–183° C.

Hydrochloride: $^1$NMR (d$_6$-DMSO) δ: 1.65 (1H, m), 1.95–2.05 (2H, m), 1.98 (3H, s, CH$_3$), 2.20 (1H, m), 2.75 (1H, m), 2.90–3.60 (7H, m), 3.88 (3H, s, OCH$_3$).

$^{13}$C NMR (d$_6$-DMSO) δ: 12.54, 26.62, 32.19, 32.82, 33.85, 49.68, 53.04, 57.07, 61.00, 156.18.

Analysis: C$_{10}$H$_{18}$N$_2$O. HCl requires C: 54.91, H: 8.76, N: 12.81; found C: 54.93, H: 8.85, N: 12.73.

Biological Activity

Radio ligand Binding

Cerebral cortex from Hooded Lister rats (Olac, UK) is homogenized in 2.5 vols ice-cold 50 mM tris buffer pH 7.7 (at 25° C.). After centrifugation at 25,000 ×g at 4° C. for 15 min the pellet is resuspended in 2.5 vols buffer and the wash repeated 3 times more. The final resuspension is in 2.5 volumes and the homogenates are stored in 1 ml aliquots at −20° C.

Incubations (total volume 2 ml) are prepared using the above buffer with the addition of 2 mM magnesium chloride in the 3H—Oxotremorine—M (3H—OXO—M) experiments. For 3H—Quinuclidinyl Benzilate (3H—QNB), 1 ml of stored membranes is diluted to 30 ml and 0.1 ml mixed with test compound and 0.27 nM (c. 25,000 cpm) 3H—QNB (Amersham International). For 3H—OXO—M, 1 ml of membranes is diluted to 6 ml and 0.1 ml mixed with test compound and 2 nM (c. 250,000 cpm) 3H—OXO—M (New England Nuclear).

Non-specific binding of 3H-QNB is defined using 1 μM Atropine sulphate (2 μM Atropine) and of 3H—OXO—M using 10 μM Oxotremorine. Non-specific binding values typically are 5% and 25% of total binding, respectively. Incubations are carried out at 37° C. for 30 min and the samples filtered using Whatman GF/B filters. (In the 3H—OXO—M experiments the filters are presoaked for 30 min in 0.05% polyethylenimine in water). Filters are washed with 3×4 ml ice-cold buffer. Radioactivity is assessed using a Packard BPLD scintillation counter, 3 ml Pico-Fluor 30 (Packard) as scintillant.

This test provides an indication of the muscarinic binding activity of the test compound. The results are obtained as IC$_{50}$ values (i.e. the concentration which inhibits binding of the ligand by 50%) for the displacement of the muscarinic agonist 3H—OXO—M and the muscarinic antagonist 3H—QNB. The ratio IC$_{50}$ (3H—QNB)/ IC$_{50}$ (3H—OXO—M) gives an indication of the agonist character of the compound. Agonists typically exhibit a large ratio; antagonists typically exhibit a ratio near to unity. The results are shown in Table 1.

TABLE 1

| Compound | [3H]-OXO-M IC$_{50}$ (nM) | [3H]-QNB IC$_{50}$ (nM) |
|---|---|---|
| E 1 | 73 | 5200 |
| E 2 | 95 | 10000 |
| E 3 | 69 | 2000 |
| E 6 | 46 | 4400 |
| E 7 | 14 | 4800 |
| E 8 | 160 | 5600 |
| E 9 | 24 | 2700 |
| E 13 | 99 | 9000 |
| E 15 | 219 | 3900 |
| E 16 | 204 | 3400 |
| E 17 | 190 | 2450 |
| E 19 | 118 | 40000 |
| E 20 | 55 | 12500 |
| E 21 | 352 | 21000 |
| E 22 | 215 | 8500 |
| E 23 | 240 | 5569 |
| E 24 | 320 | 7300 |

We claim:

1. A compound of formula (I) or a pharmaceutically acceptable salt thereof:

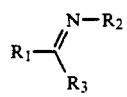
(I)

wherein R$_1$ represents

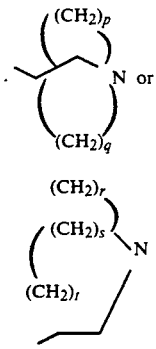

in which
each of p and q independently represents an integer of 2 to 4, r represents an integer of 2 to 4, s represents 1 or 2 and t represents 0 or 1;

R$_2$ is a group OR$_4$, where R$_4$ is C$_{1-4}$ alkyl, C$_{2-4}$ alkenyl, C$_{2-4}$ alkynyl, a group OCOR$_5$ where R$_5$ is hydrogen or R$_4$, or a group NHR$_6$ or NR$_7$R$_8$ where R$_6$, R$_7$ and R$_8$ are independently C$_{1-2}$ alkyl; and R$_3$ is hydrogen or C$_{1-4}$ alkyl, subject to the proviso that when R$_2$ is a group OCOR$_5$ or a group NHR$_6$, R$_3$ is C$_{1-4}$ alkyl.

2. A compound according to claim 1 in which R$_4$ or R$_5$ is selected from methyl, ethyl, allyl and propargyl, or R$_6$, R$_7$ and R$_8$ are methyl.

3. A compound according to claim 1 in which R$_2$ is methoxy, ethoxy, allyloxy, propargyloxy, acetoxy or dimethylamino.

4. A compound according to claim 1 in which $R_2$ is a group $OR_4$ or $NR_7R_8$ and $R_3$ is hydrogen or methyl, or $R_2$ is a group $OCOR_5$ or $NHR_6$ and $R_3$ is methyl.

5. A compound according to claim 1 in which p represents 2 and q represents 2 or 3, or the combination (r,s,t) is (2,2,0), (2,1,1), (3,1,1), (2,1,0) or (3,1,0).

6. A compound according to claim 1 having two asymmetric centers, in the exo-configuration.

7. A compound selected from:
(±) syn-1-azabicyclo[3,2,1]oct-5-yl carboxaldehyde, O-methyloxime;
(±) 1-azabicyclo[2.2.2]oct-3-ylcarboxaldehyde, O-methyloxime;
(±) trans-3-acetyl-1-azabicyclo[2.2.2]octane-O-methyloxime;
(±) syn-1-azabicyclo[3.2.1]oct-5-ylcarboxaldehyde, O-propargyloxime;
(±) syn-1-azabicyclo[3.2.1]oct-5-ylcarboxaldehyde, O-ethyloxime;
(±) trans-5-acetyl-1-azabicyclo[3.2.1]octane-O-methyloxime;
(±) exo-1-azabicyclo[2.2.1]hept-3-ylcarboxaldehyde, O-methyloxime;
(±) exo-1-azabicyclo[2.2.1]hept-3-ylcarboxaldehyde, O-ethyloxime;
(±) exo-1-azabicyclo[2.2.1]hept-3-ylcarboxaldehyde, O-propargyloxime;
(±) syn-1-azabicyclo[3.2.1]oct-5-ylcarboxaldehyde-N,N-dimethylhydrazone;
(±) trans-3-acetyl-1-azabicyclo[2.2.2]octane-O-acetyloxime;
(±) 5-propan-1-one-1-azabicyclo[3.2.1]octane-trans-O-methyloxime;
(±) exo-3-acetyl-1-azabicyclo[2.2.1]heptane-trans-O-methyloxime;
(±) exo-3-acetyl-1-azabicyclo[2.2.1]heptane-trans-O-ethyloxime;
(±) exo-3-acetyl-1-azabicyclo[2.2.1]heptane-trans-O-propargyloxime;
(±) exo-3-propan-1-one-1-azabicyclo[2.2.1]-heptane-trans-O-methyloxime;
(±) 1-azabicyclo[2.2.2]oct-3-ylcarboxaldehyde, O-propargyloxime;
(±) exo-1-azabicyclo[2.2.1]hept-3-ylcarboxaldehyde-syn-dimethylhydrazone;
syn-1-azabicyclo[2.2.1]hept-4-ylcarboxaldehyde, O-methyloxime;
4-acetyl-1-azabicyclo[2.2.1]heptane-O-methyloxime;
syn-1-azabicyclo[2.2.1]hept-4-ylcarboxaldehyde, O-propargyloxime;
(±) exo-1-azabicyclo[2.2.1]hept-3-ylcarboxaldehyde;
(±) exo-1-azabicyclo[3.2.1]oct-3-yl-carboxaldehyde, O-methyloxime; and
(±) exo-3-Acetyl-1-azabicyclo[3.2.1]octane-trans-O-methyloxime; or a pharmaceutically acceptable salt thereof.

8. A pharmaceutical composition comprising a compound of formula (I) or a pharmaceutically acceptable salt thereof, as defined in claim 1, and a pharmaceutically acceptable carrier.

9. A method of treatment or prophylaxis of dementia in mammals including humans, which comprises administering to the sufferer an effective amount of a compound of formula (I) or a pharmaceutically acceptable salt thereof, as defined in claim 1.

* * * * *